United States Patent [19]

Lehmussaari et al.

[11] Patent Number: 5,795,913
[45] Date of Patent: *Aug. 18, 1998

[54] OPHTHALMIC COMPOSITION

[75] Inventors: Kari Lehmussaari; Eija Vartiainen; Timo Reunamaki; Olli Oksala, all of Tampere; Sakari Alaranta, Kangasala; Esko Pohjala, Tampere, all of Finland

[73] Assignee: Santen Oy, Tampere, Finland

[*] Notice: The term of this patent shall not extend beyond the expiration date of Pat. No. 5,710,182.

[21] Appl. No.: 535,033
[22] PCT Filed: Mar. 29, 1995
[86] PCT No.: PCT/FI95/00167
§ 371 Date: Mar. 15, 1996
§ 102(e) Date: Mar. 15, 1996
[87] PCT Pub. No.: WO95/26712
PCT Pub. Date: Oct. 12, 1995

[30] Foreign Application Priority Data

Mar. 31, 1994 [SE] Sweden .................................. 9401109

[51] Int. Cl.⁶ .................................................. A61K 31/35
[52] U.S. Cl. .................................. 514/459; 514/912
[58] Field of Search .................................. 514/459, 912

[56] References Cited

FOREIGN PATENT DOCUMENTS 2839752  12/1995  Germany .
WO 9119481  12/1991  WIPO .
WO 9300887  1/1993  WIPO .

OTHER PUBLICATIONS

Florence Thermes et al., "Bioadhesion: The Effect of Polyacrylic Acid on the Ocular Bioavailability of Timolol", 1992, vol. 81, pp. 54–65, International Journal of Pharmaceutica.

*Primary Examiner*—Zohreh Fay

[57] ABSTRACT

The present invention is directed to an ophthalmic composition in the form of a topical aqueous solution consisting essentially of

- an ophthalmologically active agent containing basic groups,
- an ion sensitive, hydrophilic polymer containing acidic groups in an amount of 0.004 to 1.5% by weight,
- at least one salt selected from the group of inorganic salts and buffers in a total amount of from 0.01 to 2.0% by weight,
- and optionally a wetting agent and a preservative, the ratio between salt and polymer being such that the solution exhibits a viscosity of less than 1000 mpas, and the pH of the solution is 4.0 to 8.0. The composition contains a sufficient amount of polymer to provide for a controlled absorption of the drug into the eye, its viscosity having been reduced to provide for better handling characteristics.

10 Claims, 6 Drawing Sheets

OPHTHALMIC COMPOSITION

BACKGROUND OF THE INVENTION

The present invention relates to an ophthalmic composition in the form of a topical aqueous solution for human and veterinary use, as well as the use of the solution, especially for the treatment of glaucoma and ocular hypertension.

It is well known to use polymers alone or in combination with other polymers for the preparation of ophthalmic pharmaceuticals and artificial tear compositions. The inclusion of the polymer aims at increasing the viscosity of the composition so as to provide for a longer contact time with the cornea of the eye, and, for example, in connection with ophthalmic drugs, to provide for a sustained release of the drug into the eye.

For example, the U.S. Pat. Nos. 5,075,104 and 5,209,927 relate to an ophthalmic gel composition and an ophthalmic liquid composition, respectively. The first mentioned composition includes 0.25 to 8% by weight of a carboxy vinyl polymer (polymer of carbomer type), the latter 0.05 to 0.25% by weight, resulting in viscosities of the compositions ranging from 15000 to 300000, or 10 to 20000, respectively.

In the publication WO 93/17664 high viscosity, polymer containing ophthalmic compositions are disclosed containing, in combination, carboxy vinyl polymers of the carbomer type, and cellulosic polymers. According to this disclosure lower polymer concentrations can be used while still achieving the desired higher viscosity. A wide range for the concentration of polymers is given, the broadest range indicated being 0.05 to 3% by weight of carbomer, and 0.05 to 5.0% by weight of cellulose polymer. A similar two-polymer system is described in the WO-publication WO 91/19481, the system being such which gels when exposed to the pH and temperature conditions of the eye surface. In the said publication, an inclusion of up to 0.9% of salt is contemplated for the adjustment of the viscosity.

There is also a number of publications relating to pharmaceutically active ophthalmic compositions containing various polymers, i.a. carboxy vinyl polymers, at various concentrations. As tonicity regulating agents, usually non-ionic polyols are suggested so as not to interfere with the gel structure (WO 93/00887, WO 90/13284). In the publication Int. J. Pharm. 81 (1992) 59–65, aqueous compositions containing timolol maleate and 0.6% polyacrylic acid (MW 250,000), as well as the salt of timolol base with 0.6% polyacrylic acid are described, containing mannitol as tonicity regulator. The viscosity measured at low shear rates is indicated as being 45 centipoise.

In the DE-patent specification 28 39 752 ophthalmic gel compositions are described containing carboxy vinyl polymers in an amount of 0.05 to 5.0% by weight and exhibiting viscosities of 1000 to 100,000 centipoise. According to this disclosure, a small amount of sodium chloride from 0.001 to 0.5% by weight is added in order to prevent the gel from breaking down on the surface of the eye (see column 4, lines 41 ff).

SUMMARY OF THE INVENTION

The present invention is based on the discovery that the beneficial effect of ophthalmic compositions of the above type containing viscosity enhancing agents, is due to the concentration of the polymer present in the composition, rather than on the viscosity thereof. Thus one object of the invention is to provide an ophthalmic composition with a sufficiently high concentration of polymer to control the formation of the polymer film on the cornea of the eye, but which composition is still fluid enough for ocular topical application. A further object of the invention is to provide an easy-to-use eye drop formulation with improved patient compliance.

According to the invention it has now been shown that by raising the concentration of the polymer over a value where the composition normally is a gel rather than a liquid and by simultaneously lowering the viscosity thereof, it is possible to obtain a desired beneficial effect of the active agent in the eye, while simultaneously reducing any discomfort in the patient's eye, as compared to the administration of a composition in gel form. The unbroken and even polymer film still being formed on the eye facilitates the binding and retaining of water on the surface of the eye, and thus provides for an additional wetting effect while providing for a better contact and thus a controlled absorption of active agent into the eye.

According to the invention we have shown that it is the amount of polymer in the composition, rather than the viscosity of the composition as such, which are important from the point of view of obtaining good absorption of drug into the eye. This is especially evident from the tests described below. In the FIG. 3 it is shown, for example, that by using the same amount of polymer, in compositions that have different viscosities, the compositions provide for substantially the same absorption. According to the state of the art one would, however, had expected the composition with the higher viscosity to provide for the higher absorption. These results are supported also by the results presented in the FIG. 4, which show that compositions, which contain different amounts of polymer, but have the same viscosities and pH's, the absorption is stronger form the composition with the higher polymer concentration.

A further important beneficial effect is achieved by using, according to the invention, an ophthalmologically active agent which contains basic groups, such as amine groups. Such a basic agent participates in an ion exchange reaction or salt formation with a polymer containing acid groups, such as polyacrylic acid polymer. The increased retaining ionic forces between the polymer and active agent provides for a further improved delivery of the active agent. Due to the fact that the basic drug is well retained by the polymer, the dosage can be lowered and/or the daily number of administration of the drug can be reduced, if desired, without the loss of activity, and consequently the side effects can be reduced as well.

The present invention thus provides an ophthalmological composition in a liquid, easy-to-use form which provides for both an increased and prolonged absorption of active agent into the eye. The invention thus makes it possible to treat e.g. glaucoma and ocular hypertension using a once-a-day-only or less frequent regimen for administering the ophthalmological active agent and to lower the dosage clearly below the dosages presently in use.

More specifically, the object of the invention is an ophthalmological composition in the form of a topical aqueous solution consisting essentially of (%:s are of the total composition)

- an ophthalmologically active agent containing basic groups,
- an ion sensitive, hydrophilic polymer containing acidic groups in an amount of 0.004 to 1.5% by weight,
- at least one salt selected from the group of inorganic salts and buffers in a total amount of from 0.01 to 2.0% by weight, a wetting agent in an mount of 0 to 3.0% by weight, a preservative in an mount of 0 to 0.02% by weight, and water, the ratio between salt and polymer components being such that the solution exhibits a viscosity of less than 1000 mPas, and the pH of the solution is 4.0 to 8.0.

DETAILED DESCRIPTION OF THE INVENTION

Figure 1:
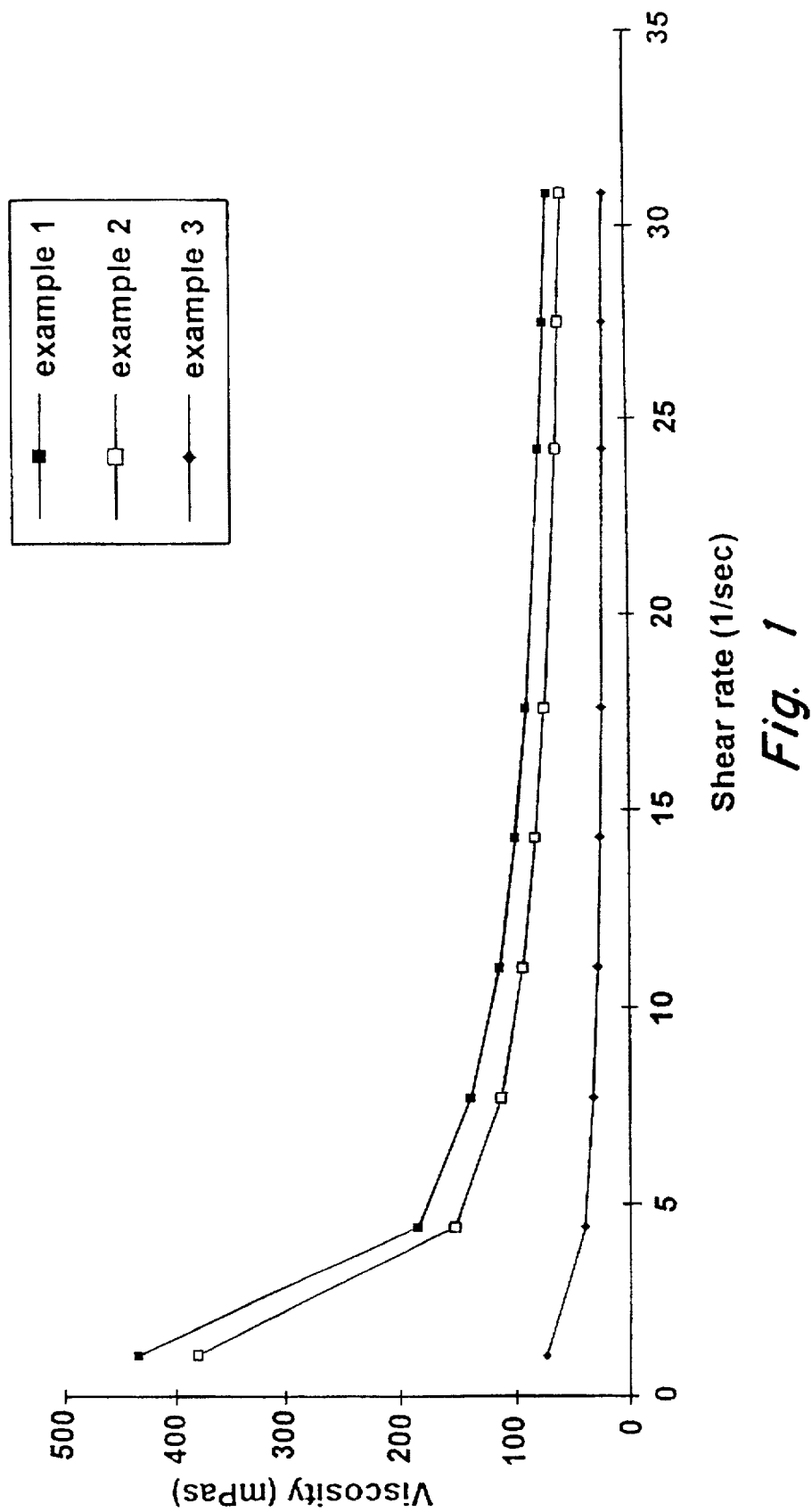
FIG. 1 is a graph of viscosity versus shear rate of the solutions described in Examples 1–3 herein.

The ion-sensitive hydrophilic polymer to be used according to the invention contains acid groups, and is typically a carboxy vinyl polymer, or hyaluronic acid. Typical representatives of carboxy vinyl polymers are the polyacrylic acid polymers, known as carbomers. Carbomers are available at different molecular weights, typically ranging from e.g. 450.000 to 4.000.000, and sold under the trade name Carbopol, e.g. Carbopol 907, 910, 934, 934P, 940, 941, 971, 971P, 974, 974P, 980, and 981, preferably Carbopol 941 and 981.

The polymer is preferably used in an amount of 0.01 to 0.8, more preferably 0.01 to 0.4, and advantageously 0.04 to 0.4% by weight.

According to the invention it has been established that it is favourable both from the view point of efficacy of the product in the target site, and of ease of application, to reduce the viscosity of the composition to a level of less than 1000 centipoise, suitably less than 800 mPas, when measured at 25° C. with a Brookfield LVDV-III type viscometer at a shear rate D of 1.1 s$^{-1}$. This object is achieved by adding to the composition a salt and/or a buffer in the specified amount, preferably in an amount of 0.01 to 1.5% by weight. As viscosity decreasing salts and buffers the following may be mentioned: sodium chloride, potassium chloride, sodium phosphates (monobasic and dibasic), sodium borate, sodium acetate, sodium citrate, equivalents or mixtures thereof. In case no salts are added, a formulation with an unacceptably high viscosity is obtained. - It is to be noted that the composition according to the invention still exhibits favourable non-newtonian properties when applied to the eye surface, despite the addition of salts.

For some purposes, for example for appearance and storage purposes, the use of a buffering salt is preferred to the use of e.g. sodium or potassium chloride as the viscosity reducing agent.

The pH of the composition is suitably from 5.0 to 8, preferably from 6.5 to 8.0. The pH of the composition is according to the invention adjusted solely by means of the amounts used of acidic polymer and basic active agent, respectively, and in such cases no additional pH-regulating agents are needed. This in turn means that the process for manufacturing the composition can be simplified.

The ophthalmologically active agent is advantageously an antiglaucoma agent, a sympathomimetic agent, a sympatholytic agent, such as a β-blocker, carbonic anhydrase inhibitor, or an antibiotic, antiinflammatoric, antiallergic agent, etc. containing a basic group, or a combination thereof. Thus according to the invention, the eye drugs contemplated may contain a primary, secondary or tertiary amino group or organoammonium or amidine attached to a chain or a ring, or a nitrogen atom(s) can be a part in various basic heterocycles, such as imidazole, imidazoline, pyridine, piperidine or piperazine. Preferably an agent active against glaucoma or effective in the treatment of increased intraocular pressure is used. A particularly preferred group of compounds is comprised of β-blocking agents having a secondary amine function such as betaxolol, carteolol, levobunolol, metipranolol, pindolol, propranolol and timolol in base form. An especially advantageous mode of the invention is such where timolol is used as its easily crystallizable S-timolol hemihydrate.

Other typical examples of basic drug molecules useful in eye therapy include tobramycin and norfloxacin (antimicrobial, antibacterial), cyclopentolate, tropicamide, atropine, phenylephrine, metaoxedrine (anticholinergic, mydriatic), pilocarpine, carbacol, ecothiopate (cholinergic), adrenaline, dipivefrin, dopamine (adrenergic), naphazoline, tetryzoline (vasoconstrictor), verapamil, nifedipine (vasodilator), apraclonidine, clonidine, medetomidine ($\alpha_2$-agonist), sezolamide (carbonic anhydrase inhibitor), cetirizine (antihistamine), as such or in their ester and prodrug forms.

Especially contemplated in the invention is the use of a β-blocking agent, such as S-timolol, especially in the from of the hemihydrate, as the only drug, or as combined with e.g. the base form of pilocarpine.

The amount of active agent in the final composition may vary, such as between 0.001 to 5% by weight, usually, however, between 0.01 to 0.5% by weight, and typically between 0.1 and 0.5% by weight, especially in the case of S-timolol hemihydrate.

According to an advantageous embodiment of the invention, the composition contains in addition, in order to enhance the wetting effect thereof, a wetting agent, preferably a polyhydric alcohol, such as glycerol. The amount of wetting agent is generally at the most 3.0, such as of the order of 0.5 to 3.0% by weight.

As preservatives, e.g. benzalkonium chloride, benzyl alcohol, mercury salts, thiomersal, chlorhexidine or the like, as such or in combination. The amount of preservative usually lies in the range of 0 to 0.02% by weight.

An advantageous composition in the form of an aqueous solution consists essentially of the following components (% being % by weight of the total composition):

timolol in the form of its hemihydrate in an amount of 0.1 to 0.5% by weight, calculated as the free base, polyacrylic acid in an amount of 0.04 to 0.4% by weight glycerol in an amount of 0.5 to 2.5% by weight sodium phosphates in an amount of 0.01 to 1.5% by weight, a preservative in an amount of 0 to 0.02%, and water, the viscosity of the composition being less than 800 centipoise and the pH of the composition being 6.5 to 8.

According to the invention, the term "consisting essentially of" is intended to mean that the composition contains only or essentially only the components listed in connection therewith. The compositions may however, in addition, contain substances, such as ophthalmologically acceptable adjuvants and additives of such a type and in such amounts as to have no essential influence on the characteristics of the composition.

The composition according to the invention is typically prepared in three stages. In the first step the polymer is dispersed in sterile water and sterilized by autoclaving. In the second step, the other ingredients, namely the active ingredient(s), inorganic salt(s), tonicity regulating agent(s), preservative(s) and any other additives, are dissolved in sterile water and sterilized by filtration on a filter (pore size e.g. 0.2 μm). In the third and last step the solution prepared in the two steps are combined aseptically and mixed until they form a homogenous solution with a low viscosity. The pH of the solution is usually adjusted by adjusting the relative amounts of active agent and polymer. Thereafter the composition is packaged in multi- or unit dose form.

The following examples illustrate the invention in more detail, without limiting the same.

EXAMPLE 1

The following composition was made:

| Composition | (g) |
|---|---|
| S-Timolol hemihydrate | 2.56 |
| Carbopol 941 | 0.95 |
| Sodium phosphate monobasic | 0.08 |
| Sodium phosphate dibasic | 1.80 |
| Glycerol | 23.0 |
| Benzalkonium chloride | 0.06 |
| Water for injection | to 1000 mL |

Carbopol 941 was dispersed in 300 mL sterile water at room temperature. The solution was sterilized in an autoclave. The autoclaved solution was cooled to room temperature (solution 1). Benzalkonium chloride, glycerol, sodium phosphate monobasic and dibasic and timolol hemihydrate were dissolved in 700 mL sterile water at room temperature and sterilized by filtration on a filter with a pore size of 0.2 μm (solution 2). In the final step the solutions prepared in the two previous steps (solution 1 and 2) were combined aseptically and mixed until they formed a homogenous low viscous solution. The pH of the solution obtained was 7.4 and its viscosity was 440 centipoise (D=1.1 s$^{-1}$). Thereafter the solution was packed in traditional eye drop bottles.

The viscosity vs. shear rate curve for the composition is shown in FIG. 1. It is to be noted that the shape of the curve shows still non-newtonian rheology despite the addition of salts.

EXAMPLE 2

The following composition was made:

| Composition | (g) |
|---|---|
| S-Timolol hemihydrate | 2.56 |
| Carbopol 941 | 0.85 |
| Sodium chloride | 0.9 |
| Glycerol | 20.0 |
| Benzalkonium chloride | 0.06 |
| Water for injection | to 1000 mL |

The solution was prepared according to the Example 1. The pH of the solution obtained was 6.9 and the viscosity of the solution was 380 centipoise (D=1.1 s$^{-1}$). Viscosity vs. shear rate curve is shown in FIG. 1.

EXAMPLE 3

The following composition was made:

| Composition | (g) |
|---|---|
| S-Timolol hemihydrate | 2.56 |
| Carbopol 981 | 1.4 |
| Sodium phosphate monobasic | 0.62 |
| Sodium phosphate dibasic | 2.85 |
| Glycerol | 23.0 |
| Benzalkonium chloride | 0.06 |
| Water for injection | to 1000 mL |

The solution was prepared according to the Example 1. The pH of the solution obtained was 6.9 and the viscosity of the solution was 70 centipoise (D=1.1 s$^{-1}$). Viscosity vs. shear rate curve is shown in FIG. 1.

EXAMPLE 4

The following composition was made:

| Composition | (g) |
|---|---|
| S-Timolol hemihydrate | 1.0 |
| Carbopol 981 | 0.65 |
| Sodium phosphate monobasic | 0.016 |
| Sodium phosphate dibasic | 0.32 |
| Glycerol | 23.0 |
| Benzalkonium chloride | 0.06 |
| Water for injection | to 1000 mL |

The solution was prepared according to the Example 1. The pH of the solution obtained was pH 6.6. The viscosity of the solution was 540 centipoise (D=1.1 s$^{-1}$).

EXAMPLE 5

The following composition was made:

| Composition | (g) |
|---|---|
| S-Timolol hemihydrate | 2.56 |
| Carbopol 941 | 2.0 |
| Sodium phosphate monobasic | 1.40 |
| Sodium phosphate dibasic | 7.42 |
| Glycerol | 16.0 |
| Benzalkonium chloride | 0.06 |
| Water for injection | to 1000 mL |

The solution was prepared according to the Example 1. The pH of the solution obtained was 6.9 and the viscosity was 600 centipoise (D=1.1 s$^{-1}$).

EXAMPLE 6

The following composition was made:

| Composition | (g) |
|---|---|
| S-Timolol hemihydrate | 5.12 |
| Carbopol 981 | 3.0 |
| Sodium phosphate monobasic | 2.0 |
| Sodium phosphate dibasic | 10.0 |
| Glycerol | 5.0 |
| Benzalkonium chloride | 0.07 |
| Water for injection | to 1000 mL |

The solution was prepared according to the Example 1. The pH of the solution obtained was 6.9 and the viscosity was 670 centipoise (D=1.1 s$^{-5}$).

EXAMPLE 7

The following composition was made:

| Composition | (g) |
|---|---|
| Clonidine (base) | 1.25 |
| Carbopol 981 | 0.70 |
| Sodium phosphate monobasic | 0.04 |
| Sodium phosphate dibasic | 0.6 |
| Glycerol | 23.0 |
| Benzalkonium chloride | 0.06 |
| Water for injection | to 1000 mL |

The solution was prepared according to the Example 1. The pH of the solution obtained was 7.0 and the viscosity was 540 centipoise (D=1.1 s$^{-1}$).

EXAMPLE 8

The following composition was made:

| Composition | (g) |
|---|---|
| Pilocarpine (base) | 20.0 |
| Carbopol 981 | 3.0 |
| Sodium phosphate monobasic | 10.6 |
| Sodium phosphate dibasic | 0.53 |
| Glycerol | 5.0 |
| Benzalkonium chloride | 0.10 |
| Water for injection | to 1000 mL |

The solution was prepared according to the Example 1. The pH of the solution obtained was 6.8 and the viscosity was 900 centipoise (D=1.1 s$^{-1}$).

By leaving out from the formulations (Examples 1–8) the benzalkonium chloride, corresponding unit-dose formulations were obtained.

Absorption of timolol into the rabbit eye (Study 1)

Figure 2:
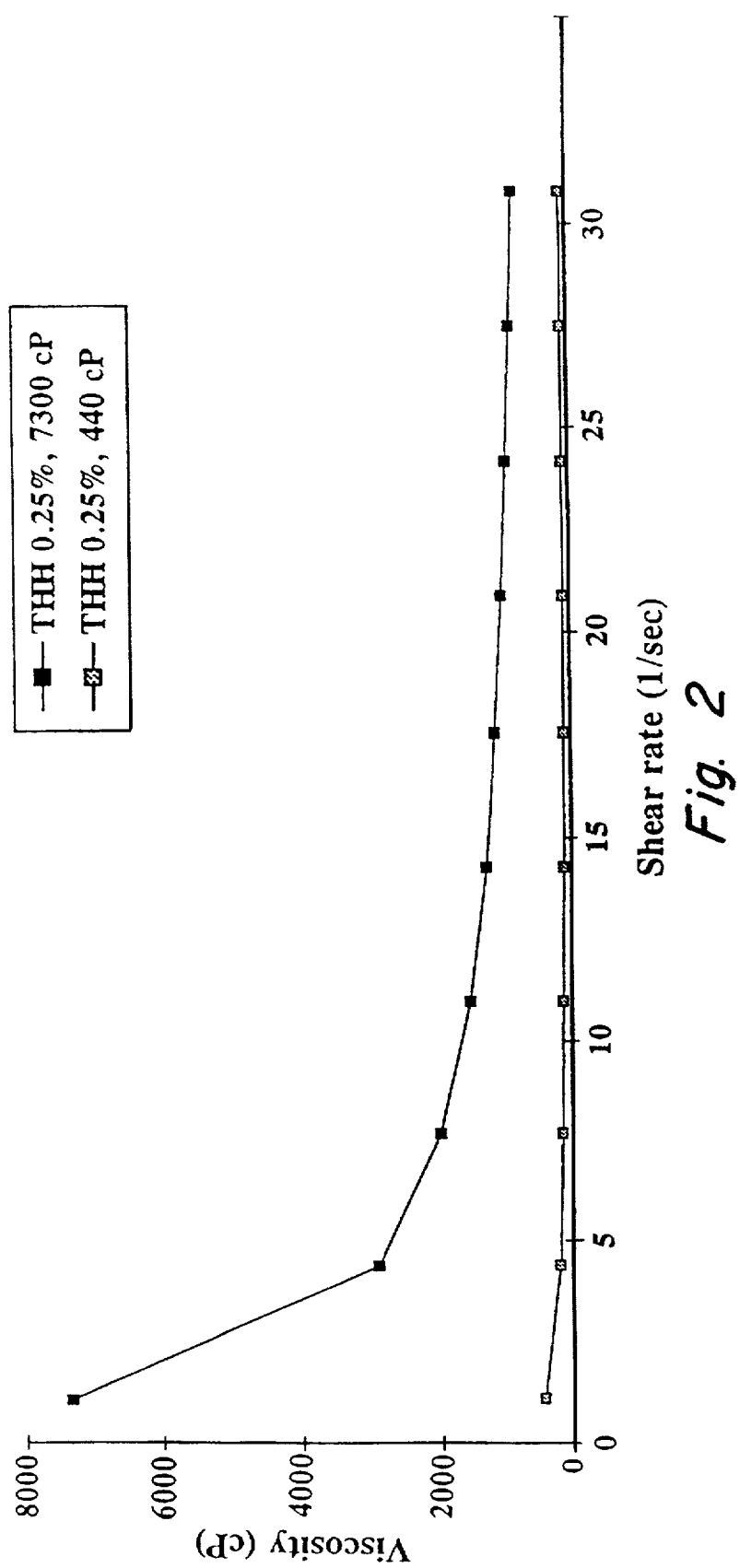
FIG. 2 is a graph of viscosity versus shear rate of the solutions compared in Study 1 described herein.

An ophthalmic formulation (Example 1), which is a typical example of this invention, was instilled into a rabbit eye (n=6). The concentration of timolol in the aqueous humor was measured after ½ and 1 hours using HPLC. The reference product contained the same amount of carbopol, timolol and preservative, benzalkonium chloride, but did not contain any inorganic salt(s). The viscosity of the reference product was much higher (7300 centipoise, D=1.1 s$^{-1}$). The viscosity curves of the products are shown in FIG. 2.

Figure 3:
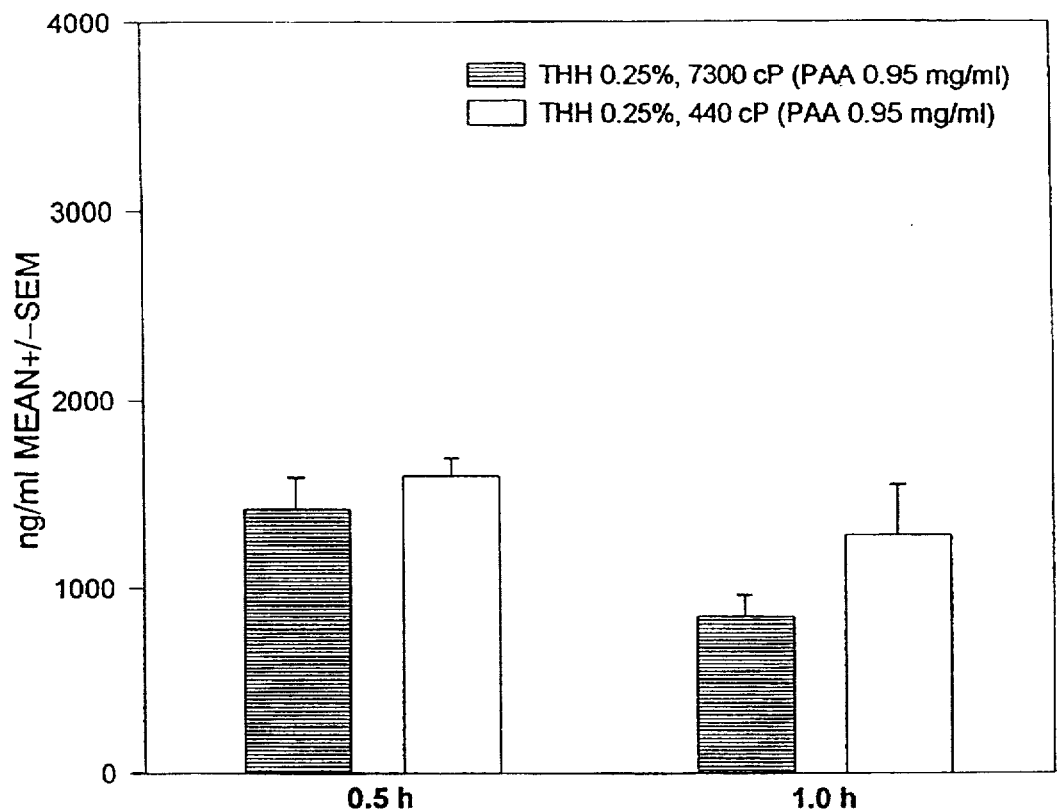
FIG. 3 is a bar graph of concentration versus absorption time of the solutions compared in Study 1 described herein.

The timolol concentrations in the aqueous humor in rabbits are shown in FIG. 3. According to FIG. 3, the absorption of timolol in rabbits eye was equal despite the different viscosities.

Absorption of timolol into the rabbit eye (Study 2 and 3)

Figure 4:
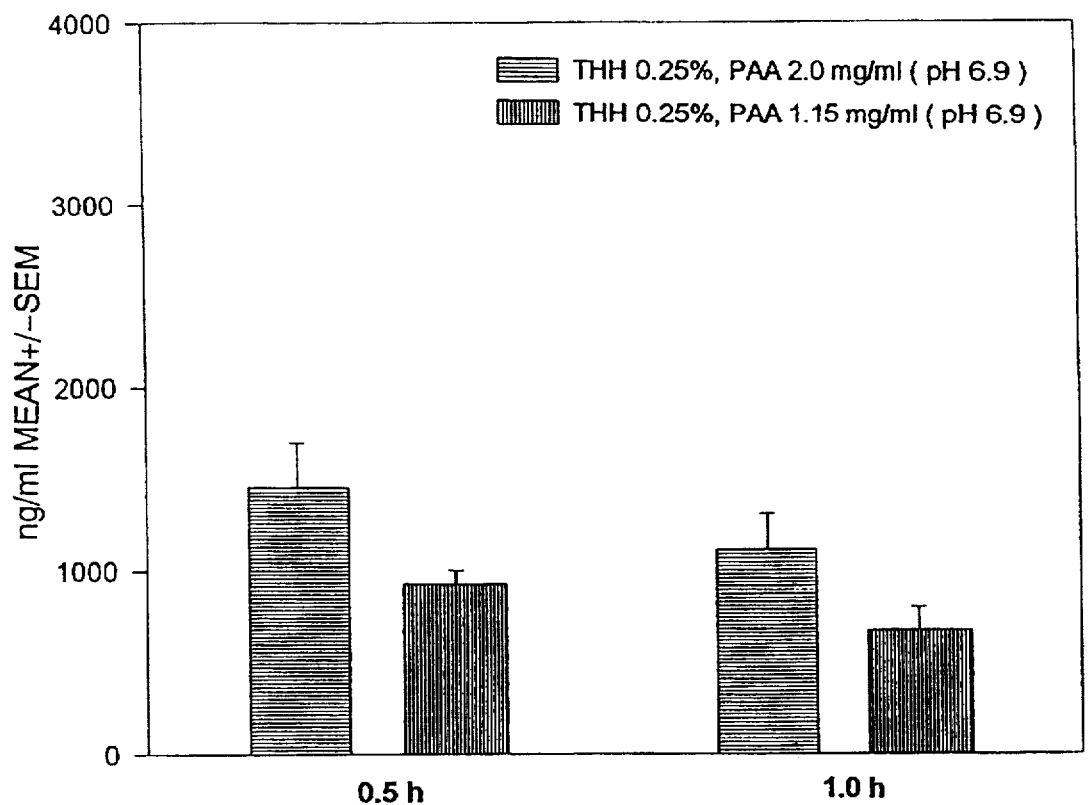
FIG. 4 is a bar graph of concentration versus absorption time of the solutions used in study 4 described herein.
Figure 5:
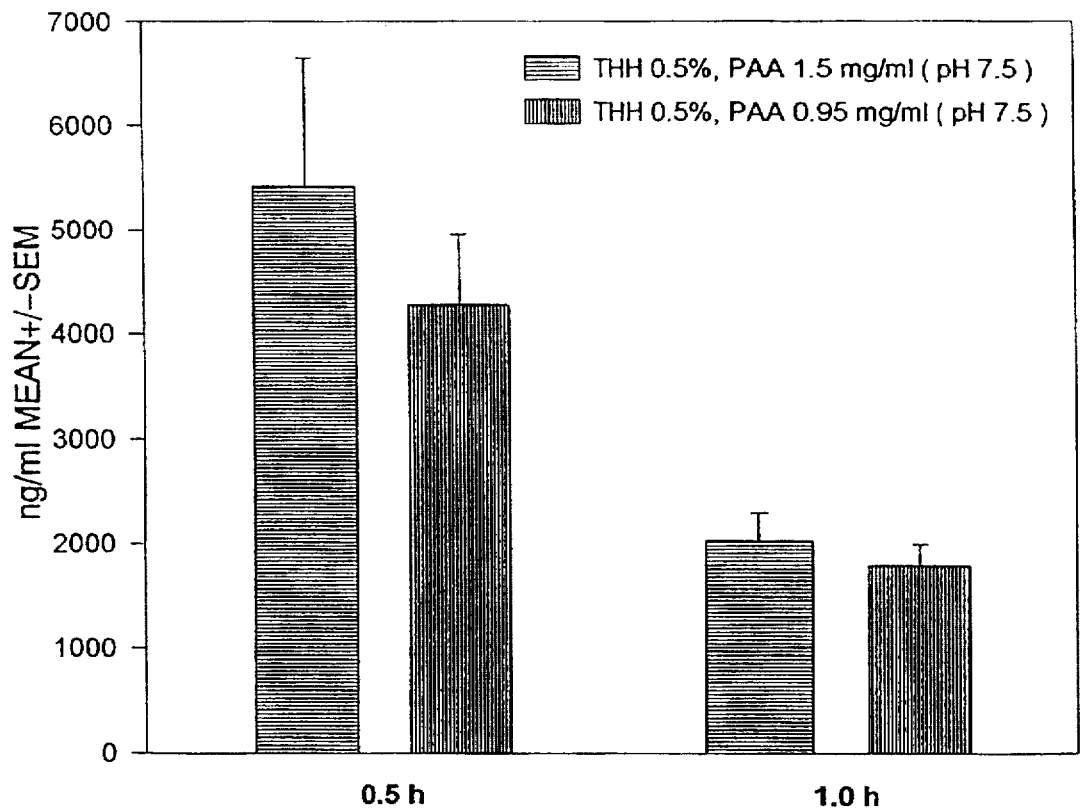
FIG. 5 is a bar graph of concentration versus absorption time of the solutions used in study 5 described herein.

Timolol solutions were installed into a rabbit eye. The administered timolol solutions had the same pH and viscosity, but the solutions contained different amounts of polyacrylic acid (Carbopol 941). The concentration of timolol in the aqueous humor was measured after ½ and 1 hours using HPLC. The timolol concentrations in the aqueous humor in rabbits are shown in the FIG. 4 and 5. According to FIG. 4 and 5, the absorption of timolol in rabbit eye depend on the concentration of the polymer used.

Stability of the timolol-polyacrylic acid solution

Figure 6:
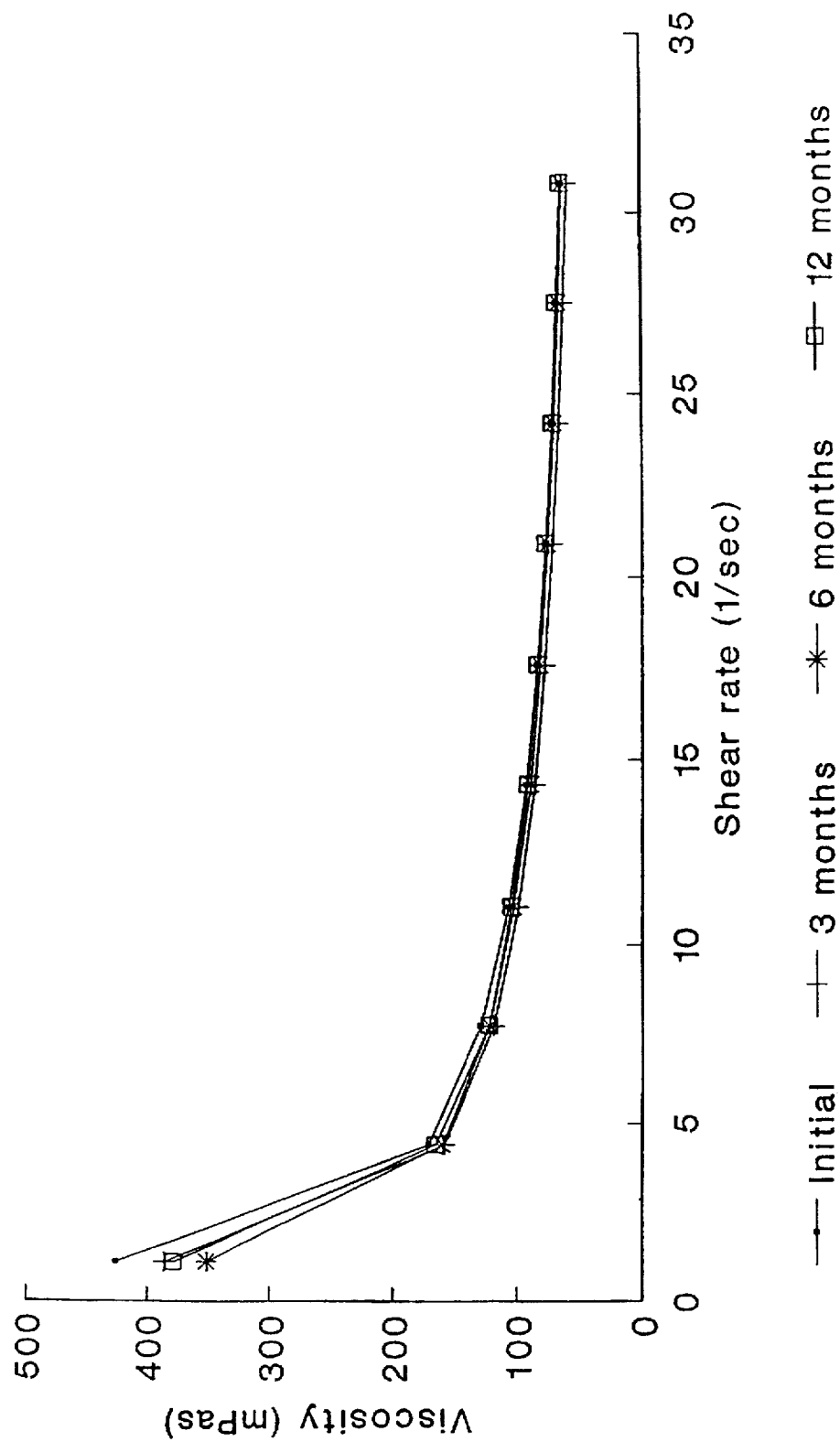
FIG. 6 is a graph of viscosity versus shear rate of a solution in accordance with Example 1 taken at various times after storage at room temperature.

An ophthalmic formulation (Example 1), which is a typical formulation of this invention, was stored at room temperature for 12 months. The viscosity of the timolol-polyacrylic acid solution was measured after different time intervals with a Brookfield LVDV-III type viscometer at room temperature. The viscosity vs. shear rate curves are shown in FIG. 6. The results show that the viscosity of the timolol-polyacrylic acid-solutiom remained stable even after one year of storage.

We claim:

1. Ophthalmic composition in the form of a topical aqueous solution consisting essentially of:

an ophthalmologically active agent containing basic groups, an ion sensitive, hydrophilic polymer containing acidic groups in an amount of 0.004 to 1.5% by weight, at least one salt selected from the group of inorganic salts and buffers in a total amount of from 0.01 to 2.0% by weight, a wetting agent in an amount of 0 to 3.0% by weight, a preservative in an amount of 0 to 0.02% by weight, as well as water, the ratio between salt and polymer being such that the solution exhibits a viscosity of less than 1000 centipoise, and the pH of the solution is between about 4.0 and about 8.0.

2. The composition of claim 1, wherein the polymer is present in an amount of from 0.01 to 0.8 by weight and is selected from the group consisting of carbopol 907, 910, 934, 934P, 940, 941, 971, 971P, 974, 974P, 980 and 981.

3. The composition of claim 1 wherein the wetting agent is glycerol.

4. The composition of claim 3, wherein the amount of glycerol is 0.5 to 2.5% by weight.

5. The composition of claim 1 or 2, wherein the sale is selected from the group consisting of sodium chloride, potassium chloride, sodium phosphates, sodium borate, sodium acetate, sodium citrate and mixtures thereof.

6. The composition of claim 1 or 2, wherein the viscosity is less than 800 centipoise.

7. The composition of claim 1 or 2, having a pH of 5.0 to 8.0.

8. The composition of claim 1, wherein the ophthalmologically active agent is selected from the group consisting of antiglaucoma agents, symphathoimimetic agents, sympatholytic agents, P-blockers, carbonic anhydrase inhibitors, antibiotics, antiinflammatoric agents, antiallergic agents and mixtures thereof.

9. The composition of claim 8, wherein the active agent is selected from the group consisting of betaxolol, carteolol, levobunolol, metipranolol, pindolol, propranolol and timolol, pilocarpine and mixtures thereof.

10. The composition according to claim 1, consisting essentially of:

timolol hemihydrate in an amount of 0.01 to 0.5% by weight;

polyacrylic acid in an amount of 0.04 to 0.4% by weight;

glycerol in an amount of 0.5 to 2.5% by weight, sodium phosphates in an amount of 0.01 to 1.5% by weight, a preservative in an amount of 0 to 0.02%, and water the viscosity of the solution being less than 800 centipoise and the pH of the solution being 6.5 to 8.

* * * * *